(12) United States Patent
Warkentine et al.

(10) Patent No.: US 8,172,775 B2
(45) Date of Patent: May 8, 2012

(54) JOINT IMPLANT PLACEMENT

(75) Inventors: Blaine Warkentine, Royersford, PA (US); Björn Spies, St. Georgen (DE)

(73) Assignee: Brainlab AG, Feldkirchen (DE)

( * ) Notice: Subject to any disclaimer, the term of this patent is extended or adjusted under 35 U.S.C. 154(b) by 493 days.

(21) Appl. No.: 12/407,031

(22) Filed: Mar. 19, 2009

(65) Prior Publication Data

US 2009/0240169 A1  Sep. 24, 2009

Related U.S. Application Data

(60) Provisional application No. 61/039,561, filed on Mar. 26, 2008, provisional application No. 61/043,906, filed on Apr. 10, 2008.

(30) Foreign Application Priority Data

Mar. 19, 2008 (EP) .................................. 08153031
Apr. 8, 2008 (EP) .................................. 08154210

(51) Int. Cl.
*A61B 5/103* (2006.01)
*A61B 5/117* (2006.01)

(52) U.S. Cl. ........................................ 600/587; 600/595
(58) Field of Classification Search .................. 600/587, 600/595
See application file for complete search history.

(56) References Cited

U.S. PATENT DOCUMENTS

| 5,828,770 A | 10/1998 | Leis et al. |
| 6,450,978 B1 | 9/2002 | Brosseau et al. |
| 2004/0030245 A1 | 2/2004 | Noble et al. |
| 2006/0064043 A1 | 3/2006 | Goeggelmann et al. |
| 2007/0066917 A1 | 3/2007 | Hodorek et al. |
| 2007/0179626 A1 | 8/2007 | de la Barrera et al. |
| 2007/0185498 A2 | 8/2007 | Lavallee |
| 2007/0219561 A1 | 9/2007 | Lavallee et al. |

FOREIGN PATENT DOCUMENTS

WO  01/78015  10/2001

*Primary Examiner* — Jeffrey G Hoekstra
(74) *Attorney, Agent, or Firm* — Renner, Otto, Boisselle & Sklar, LLP

(57) ABSTRACT

Method for planning implant placement, the implant comprising a first implant in a first limb and a second implant in a second limb, the first and the second implant forming an artificial structure joining the first and second limb, the method comprising the steps:
  a) providing a first limb data set representing a first reference system in which the first limb is fixed;
  b) providing a second limb data set representing a second reference system in which the second limb is fixed;
  c) providing a representation of the implant for the head of the second limb in a known position in the second reference system;
  d) providing relative pose data representing a plurality of different relative positions and/or orientations, referred to as relative poses, of the first and second reference system;
  e) determining a data set representing a plurality of envelope points, said envelope points being generated by calculating the locations of a point of the second implant representation in the first reference system for the plurality of relative poses; and
  f) placing a representation of the first implant in the first reference system by adjusting and/or matching pose of the representation of the first implant to the plurality of envelope points.

7 Claims, 5 Drawing Sheets

JOINT IMPLANT PLACEMENT

RELATED APPLICATION DATA

This application claims the priority of U.S. Provisional Application No. 61/039,561 filed on Mar. 26, 2008 and U.S. Provisional Application No. 61/043,906 filed on Apr. 10, 2008, which is hereby incorporated in its entirety by reference.

FIELD OF THE INVENTION

The present invention relates to a method for planning a placement of an implant. The implant comprises at least two implants, a first implant and a second implant. Both implants represent parts of a joint. The joint joins anatomical limbs. The first and the second implants form an artificial structure for joining the first and the second limb.

The present invention is in particular directed to the planning of the placement of such an implant in case of no deformity of the anatomical joint or a moderate deformity of the anatomical joint. The determination of a deformity of an anatomical joint is treated by the priority patent application called "Method and system for determination of a degree of deformity of an anatomical joint". EP 08 153 031.1, the content of which is incorporated by reference.

BACKGROUND OF THE INVENTION

The assessment or determination of a degree of deformity of a knee joint or any other anatomical structure joining two limbs assist the planning and performing of surgery, alleviates possible complications, and fosters successful rehabilitation.

In cases of mild deformities of a knee joint, the knee joint is suitable for total knee arthroblasty (TKA), for instance.

Determination of structural anatomic features require the acquisition of locations and/or orientations of anatomic objects, such as limbs relative to a spatial coordinate system or operating space.

A locating or tracking device may be used to determine a pose (position and/or orientation) of an anatomical object in a three-dimensional coordinate system or operating space by means of an array of activated markers attached to the object. Herein, a position and/or orientation is an example for a pose. By receiving signals transmitted from the markers with a sensor or sensors in different poses (spatial positions and/or orientations) the pose (position and orientation) of the marker array and thus the pose (position and/or orientation) of the anatomical object to which the marker array is attached to may be determined.

An example of a system for tracking the spatial position and angular orientation of an object may be found in U.S. Pat. No. 5,828,770.

The pose (position and/or orientation) of an object in space is referred to as the pose of the object.

The following prior art documents are cited:
M. E. Nadzadi, M S; J. K. Nielsem, M S; S. B. Murphy, M D, smith and nephew Memphis, Tenn. Intact Knee Passive Kinematics and Ligamentous Stability Measured by a Novel Navigation System; and
M. E. Nadzadi, M S; J. K. Nielsern, M S; S. B. Murphy, M D, smith and nephew Memphis, Tenn. A Novel Method for Measuring Intact Knee Joint Laxity and Kinematics Using Computer Assisted Surgical Navigation Tools.

An object of the present invention is to plan the placement of an implant in such a manner that movement of the joint after implantation corresponds to the movement of the replaced anatomical joint.

In particular, in case of a deformity of the anatomical joint to be replaced, the influence of a pre-operative deformity on the movement of the joint is preferably reduced due to the planning according to the invention.

SUMMARY OF THE INVENTION

The present invention is related to a method for planning implant placement. In more detail, the placement of a first and second implant is planned. The first and second implant is meant to replace in particular a part of a first and second anatomical limb. In particular that structure which is close to the joint. In other words, the placement of an artificial joint (artificial structure) is to be planned such that the artificial joint replaces an anatomical joint.

The method comprises in particular the step of providing a first limb data set. The first limb data set represents a first reference system in which the first limb is fixed, i.e. has a fixed spatial position relative to the reference system. Preferably, a corresponding second limb data set is provided. The second limb data set represents a second reference system in which the second limb is fixed. The first and second limb data set may be for instance generated by detecting a reference array attached to the first limb and second limb, respectively. By detecting the reference arrays and by detecting landmarks at the limb, characteristical positions of the limb, in particular the position of a characteristic axis of the limb in the respective reference system may be determined and the corresponding data may provided to be used by the method according to the present invention.

Furthermore, preferably a representation of a second (virtual) implant is provided. The representation of the second implant comprises in particular the shape and/or size of the second implant, in particular, the shape of the surface of the second implant. This representation of the second implant is preferably provided at a predetermined (known) position in the second reference system. In other words, preferably, a particular location of the second implant is a starting point of the planning procedure according to the present invention. This particular location may be determined by an operator or user of the method according to the present invention, for instance a surgeon (e.g. by an input operation in the computer). According to another embodiment, the second implant has a particular position relative to characteristic landmarks or a characteristic axis of the second limb. According to another embodiment, a proposal for a position of the second implant is given by the method according to the invention. Preferably, this proposal may be changed by the user.

Preferably, relative pose data are provided and in particular used by the present invention to perform a determination. The relative pose data describes a plurality of relative poses of the first and second reference system. These relative pose data may be generated by moving the anatomical limbs relative to each other, for instance by performing a flexion or an extension movement. The relative poses of the first and second reference system may be described by the relative poses of characteristic axes of the limbs. An axis of the limb is in particular a characteristical axis of the limb along the extension of the limb.

Based on the provided data sets, based on the provided representation of the second implant at a predetermined position (including at least the location of at least one point of the second implant) in the second reference system and based on the provided relative pose data preferably a determination step is performed. This determination step determines a plurality of envelope points. For this purpose preferably, location data describing the location of at least one point of the second implant is provided. Preferably, the location data are included in the representation data which represent the second implant. Preferably, this at least one point is at the surface of the second implant. Preferably, this at least one point, is a point where typically a contact between the first implant and the second implant should occur in case of relative movement of the implants after implantation of the implants. In a typical case, there are two contact points on the surface of the second implant. Thus, preferably, the location of two contact points are provided in the reference system of the second limb. The aforementioned location of the at least one point (e.g. surface point and/or contact point) is known in the second reference system. Based on the provided pose data and by using the first and second reference system provided by the first limb data set and the second limb data set, the location of the at least one point (e.g. surface point and/or contact point) in the first reference system may be calculated for each of the plurality of relative poses. As a consequence of this calculation, a plurality of points are generated in the first reference system. These points are called envelope points. If an sufficient number of envelope points is generated, an envelope curve may be described. According to the method, in a further step, a (virtual) representation of the first implant is virtually placed so that the first implant is adjusted with respect to the plurality of envelope points. The term adjusting means here in particular, that the first implant virtually contacts or matches the envelope points as good as possible. That is, the distance between the first implant and the envelope point is preferably minimized by using for instance least square fit methods. Preferably, the distance is 0 or larger than 0. According to an embodiment, the distance is not negative, i.e. the first implant does not partially penetrate a curve represented by the envelope points.

According to a further embodiment, a plurality of representations of first implants is provided. For instance, in a data base, characteristical data of first implants are stored, for instance size and shape of the implants. From these pluralities of virtual implants, those are selected, for which the best adjustment or matching to the envelope point can be achieved. For instance, those are selected, for which the aforementioned least square fit achieves the best fit result. In other words, preferably, that implant representation is selected, which fits to the envelope points in the best manner. The term "fitting" means for instance abutting to the envelope points or snuggly fitting in a curve described by the envelope points.

Preferably, the envelope points are generated by movement of the limbs in case of no deformity or moderate deformity. It is preferred that after implantation of the implants, the artificial joint performs a movement of no or moderate deformity even if the anatomical joint exhibited a significant pre-operative deformity provided the significant deformity may be corrected to a moderate deformity by applying an external force to the anatomical joint. For this purpose, the envelope points are preferably provided in a manner which represent a movement of the joint in case of no or moderate deformity.

For this purpose, the deformity may be determined beforehand as described in the parallel application. In particular, it may be determined to what degree (correction degree) the deformity may be corrected by applying an external force. This degree of correction may be used in order to calculate the envelope points in accordance to the invention. This calculation may be, in a first step, based on uncorrected envelope points which are generated by an uncorrected movement of the limbs. This uncorrected envelope points are then, in a second step, corrected based on the determined correction degree. The correction degree is provided to the method of the present invention and may be determined as described in the parallel application.

The correction degree may be described by a vector which describes the change of location of the first and second limb axis due to the external force in the first and second reference system, respectively. This correction vector is used to correct the relative pose of the first and second reference system to each other in case of correction. This correction vector is not only applied for instance in one of the relative poses in which the correction has been measured, for instance in the relative pose of full extension but preferably for all of the determined plurality of relative poses. In this manner, a plurality of corrected relative poses are determined. Based on these corrected relative poses, the corrected envelope points are calculated.

The connection of the relative pose at the reference system results in a connection of the location of the surface and/or contact points in the first reference system.

Alternatively, the corrected envelope points may be generated by applying a correcting force during relative movement of the limbs.

As will be described in more detail below, the first limb is in particular the femur and the second limb is the tibia. Of course, it is possible to exchange the tibia and the femur in the aforementioned embodiment such that the second limb is the femur and the first limb is the tibia. For the relative movement, preferably, flexion and/or extension movement is applied. Preferably, the envelope points are generated in a manner such that a relative rotation of the first limb relative to the second limb is within a predetermined degree. This may be preferably controlled by detecting a rotation of the first and second reference array (fixed to the first and second limb, respectively) relative to the limb axes.

Preferably, according to the present invention, for each envelope point the corresponding degree of rotation is detected and stored. Preferably only those envelope points are used for the placement of the representation of the first implant which fulfill the condition to be generated within the predetermined range of rotational angle.

For placing the representation of the first implant, i.e. for placing the virtual first implant in the first reference system with respect to the envelope points, preferably a virtual displacement, in particular a translational movement of the first implant along the axis of the first limb is performed. This translational movement is preferably combined with a tilting movement of the first implant with respect to the axis of the first limb.

The present invention is also directed to a program which performs at least a part of the aforementioned steps when running on a computer or when loaded into a computer. Furthermore, the present invention is directed to a system which comprises a computer on which the aforementioned program runs or is loaded. Additionally, the system comprises preferably a detector which detects reference arrays and/or pointers in order to gather the data necessary for performing the method. In particular, reference arrays attached to the limbs and/or pointers for detecting landmarks are detected by the detector and the corresponding detection signals are input in the computer in order to be processed in accordance with the program steps. The system is in particular constituted as a navigation system in order to allow image guided surgery.

DETAILED DESCRIPTION OF THE DRAWINGS

The present invention is directed to the situation of a moderate pre-operative deformity of the relative poses of limbs. In the following, this will be explained for an example in which the limbs are the tibia and the femur. In particular, the embodiment relates to elimination of the deformity by the surgeon from force, release, osteophyte removal or any combination of the three. Preferably, the femur is matched to the virtual tibia in extension. The present embodiment allows the surgeon to allocate 1 mm to 3 mm of laxity that he would like to produce by essentially raising the distal femoral cut by this amount. In particular, this allows the surgeon to customize the desired laxity in extension in relation to his/her requirements and the patients compliance in regards to the soft tissue envelope.

Furthermore, preferably, the limbs are relatively moved to take them through a range of motion. This is done in order to automatically plan femoral sizing (sagittal) and rotation (axial) based upon kinematics matched anteriorly to the registered points of the anterior cortex of the femur. Preferably, best fit analysis to the kinematics is achieved with the ability to choose between best sizes by the surgeon. Preferably, a small and larger size are offered and the surgeon chooses and can move the implant more anteriorly or posteriori or flex a bit to customize just a bit more if he/she really needs to.

Figure 1:
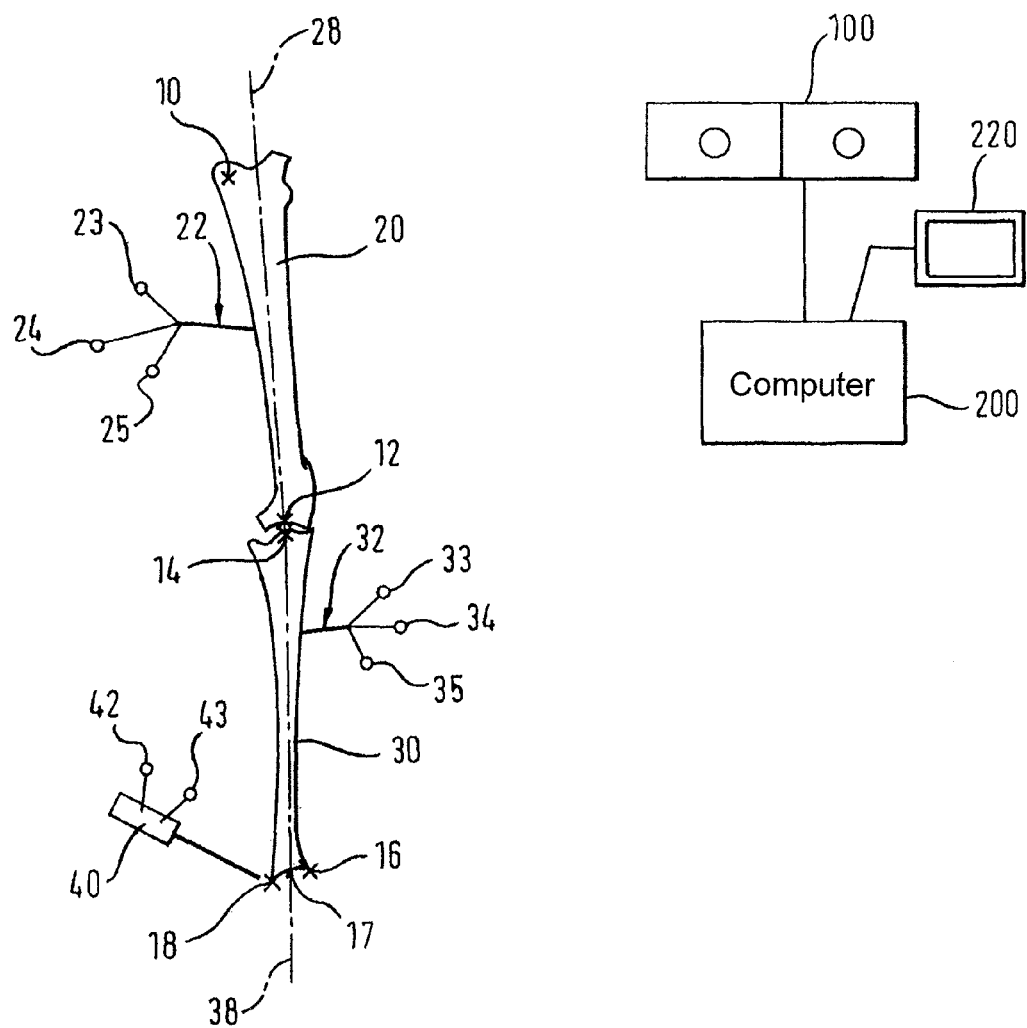
FIG. 1 shows an embodiment according to the present invention which allows detection of the relative pose of the femur reference system and the tibia reference system, in particular the relative pose of the femur axis and the tibia axis.

FIG. 1 shows schematically the tibia and the femur. Several points, in particular landmarks are acquired beforehand, in order to define axis for the femur and the tibia. In particular, the center 10 of rotation to the femoral head is calculated based on movements of the femur. Furthermore, the center of malleolus 17 is acquired by detecting location of the medial and lateral landmarks 16 and 17, e.g. by means of a pointer. In particular, an anterior posterior axial rotation is adjusted for the tibia. Preferably, an incision is made and the knee is cleaned of as many ostheophytes as possible. Additionally, the proximal tibia mechanical axis is registered. Furthermore, preferably the reference arrays 22 and 32 are fixed at the femur and the tibia, respectively. The markers 23, 24 and 25 of the reference array 22 is preferably detected by a camera or detector 100 which is connected to a computer 200 having a monitor 220. In the same way, the markers, 33, 34, and 35 of the reference array 32 is detected. Preferably, a reference system is assigned to each reference array. In these reference systems, the limbs have a fixed position, respectively. The proximal tibial mechanical axis 38 and the distal femoral mechanical axis 28 is registered based on detection of the aforementioned landmarks and points shown schematically as 10, 12, 14, 16, 17, 18 in FIG. 1. Additional landmarks may be acquired.

The landmarks are in particular detected by using a so-called pointer 40 shown schematically in FIG. 1. The pointer 40 has preferably at least two markers 42 and 43 also detected by the detector 100. The relative spatial position between the tip of the pointer and the markers 42 and 43 are known to the computer system. The same is for the relative position of the markers of the reference array 22 and the reference array 32.

Preferably, the relative positions are characteristic so that the navigation system consisting at least of the elements of the computer 200, the monitor 220 and the detector 100 may identify the reference arrays and the pointers.

Preferably after registration of the femur axis 28 and the tibia axis 38, the surgeon attempts to reduce the deformation of the limb joint as close as possible. For this, he preferably use this computer guidance. How a computer guidance may be realized in order to achieve this goal is described in the parallel application named "Method and system for determination of a degree of deformity of an anatomical joint". This parallel application is herewith incorporated by reference. This parallel application describes the measurement of deformation. The measurement results may be displayed in order to guide the user.

Preferably, the relative pose of the femur axis to the tibia axis (e.g. in a sagittal and/or coronal plane) represents the deformity and is measured in degrees. Preferably, a predetermined degree is fixed representing a limit within which the surgeon has to correct the deformity in order to apply the embodiment according to the present invention. Preferably, such a predetermined limit is below 10 degrees, preferably, less than 5 degrees, even more preferably about 3 degrees. Preferably, the present invention is applied if there is no deformity, a moderate deformity or a deformity which may be corrected (by applying force) to be only a moderate deformity.

Preferably, the relative pose of the femur axis to the tibia axis is stored in the computer 200 in order to represent a basis for the further calculation. In this way, a data set representing a reference system in which the femur is fixed is provided. In particular, the pose of the first limb axis, which is e.g. a femoral axis, is known in the reference system defined by the reference array 22. Additionally, preferably, the pose of the second limb axis, which is e.g. a tibia axis, is known in the second reference system, by a reference system defined by the reference array 32 fixed to the tibia.

In this way, a first limb data set and a second limb data set is achieved.

Figure 2:
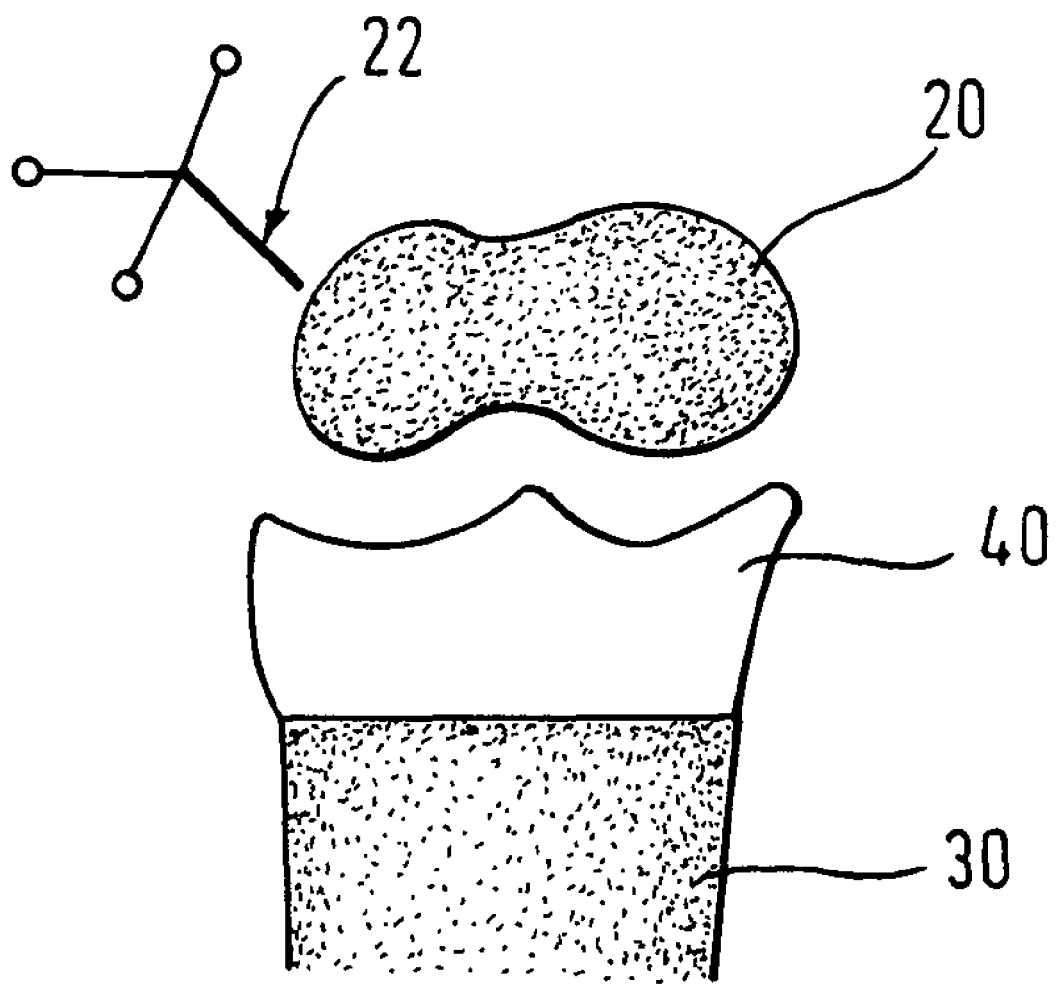
FIG. 2 shows placement of a tibia implant.

Based on the aforementioned first limb data set and second limb data set, an implant placement may be planned in accordance with the invention. The planning procedure may be performed as follows. It is planned to place an implant which replaces the tibial head close to the joint at a known position. This is called the second implant or tibia head implant. This virtual situation is schematically shown in FIG. 2 for 90° flexion. The implant head 40 is virtually placed close to the joint between the femur 20 and tibia 30.

As mentioned before, the virtual situation which represents a basis for the calculation is a situation where preferably there is no deformation or a deformation that has been reduced beforehand, e.g. by applying a force, to be within an acceptable degree. Thus, the final result of the calculation to be described in the following, will be a virtual placement of the implants at those locations which result in an undeformed knee joint or at least which result in a deformation which is within a preferred or predetermined range. The virtual placement of the second implant may be done by the surgeon and the pose of the second implant in the reference system of the tibia and in particular relative to the tibia axis represents data which is input in the planning method of the present invention. These data are a representation of the second implant in a known position in the second reference system (tibial reference system).

Preferably, the present invention and in particular a program based on the present invention is constituted to place the virtual tibial implant relative to the tibial mechanical axis point and/or other tibial landmarks and additionally preferably to match the femoral implant, in particular the cruciate retaining implant within the data base for the middle of the tibial implant.

The above-mentioned method of tibia implant placement is preferred because the middle of the knee is not subject to bone loss and articular cartilage differences as the plateaus are.

Preferably, the planning software allows to change the shaping size of the implant (tibia implant and/or femur implant). Preferably, the placement of the implant is virtually performed in extension of the limbs.

According to a preferred embodiment, first virtually the tibia implant is placed and then second according to a preferred embodiment, the femur implant is placed. The femur implant is preferably placed just proximal to the virtual tibia provided both limbs are in extension. For placing the femur implant relative to the tibia implant so-called envelope points are used as described later.

It is up to the surgeon whether he would like to optimize the laxity in extension. If the joint is stiff than the surgeon would for instance pick a range of 1 to 5 mm, preferably 2 to 3 mm of laxity and if the joint is compliant and loose than perhaps 0 mm to 1 mm of laxity would be required as a decision process for the surgeon. This essentially lifts the distal femur resection by this desired amount. This decision process is up to the surgeon and the pose of the femur implant and tibia implant relative to each other represents data input into the data processing method according to the present invention.

According to the embodiment of the invention not just one relative pose, for instance in extension, is provided as data to the data processing method but a plurality of relative poses. In order to generate the data of relative poses, preferably, the surgeon moves the limbs relative to each other. For instance, the surgeon takes the limb through a range of motion. During the motion, the reference arrays 22 and 34 are detected by the detector 100. By detecting the reference arrays, a plurality of relative poses of the tibia reference system relative to the femur reference system, i.e. of the second reference system relative to the first reference system, are provided. Based on the known position of at least one implant (e.g. tibia implant 40) in the respective reference system or to be more accurate, based on at least one known location of at least one point of the at least one implant, so-called envelope points, may be calculated as explained in the following.

For the generation of the relative poses, a surgeon may for instance perform flexion of the joint for instance at least about 90 degrees. In praxis, a flexion of 90 degrees may be possible since the patients have no deformity or no significant deformity as described above.

According to a particular embodiment, the relative poses of the reference systems are stored for instance in regular intervals of flexion. The intervals may be for instance in the range of 1 to 20 degrees, preferably in the range of 5 to 15 degrees, preferably about 10 degrees. By means of the detector 100, the reference arrays are detected and the relative poses are detected and stored in the computer 100 in order to use these relative pose data for the determination of the aforementioned envelope points.

As mentioned above, at least one location of at least one point of the implant is known in the reference system in which the implant has a fixed position. For instance a surface point of the tibia implant is known in the tibia reference system (second reference system). Based on the relative pose data which describe the relative poses of the reference systems for each of the relative poses, the location of the tibia surface point in the other reference system, i.e. in the reference system of the femur, may be calculated for each of the relative poses. In this way, a plurality of locations of the surface point in the other reference system, i.e. in the reference system of the femur, is calculated. These plurality of locations generated by one and the same surface point are called envelope points.

Figure 3:
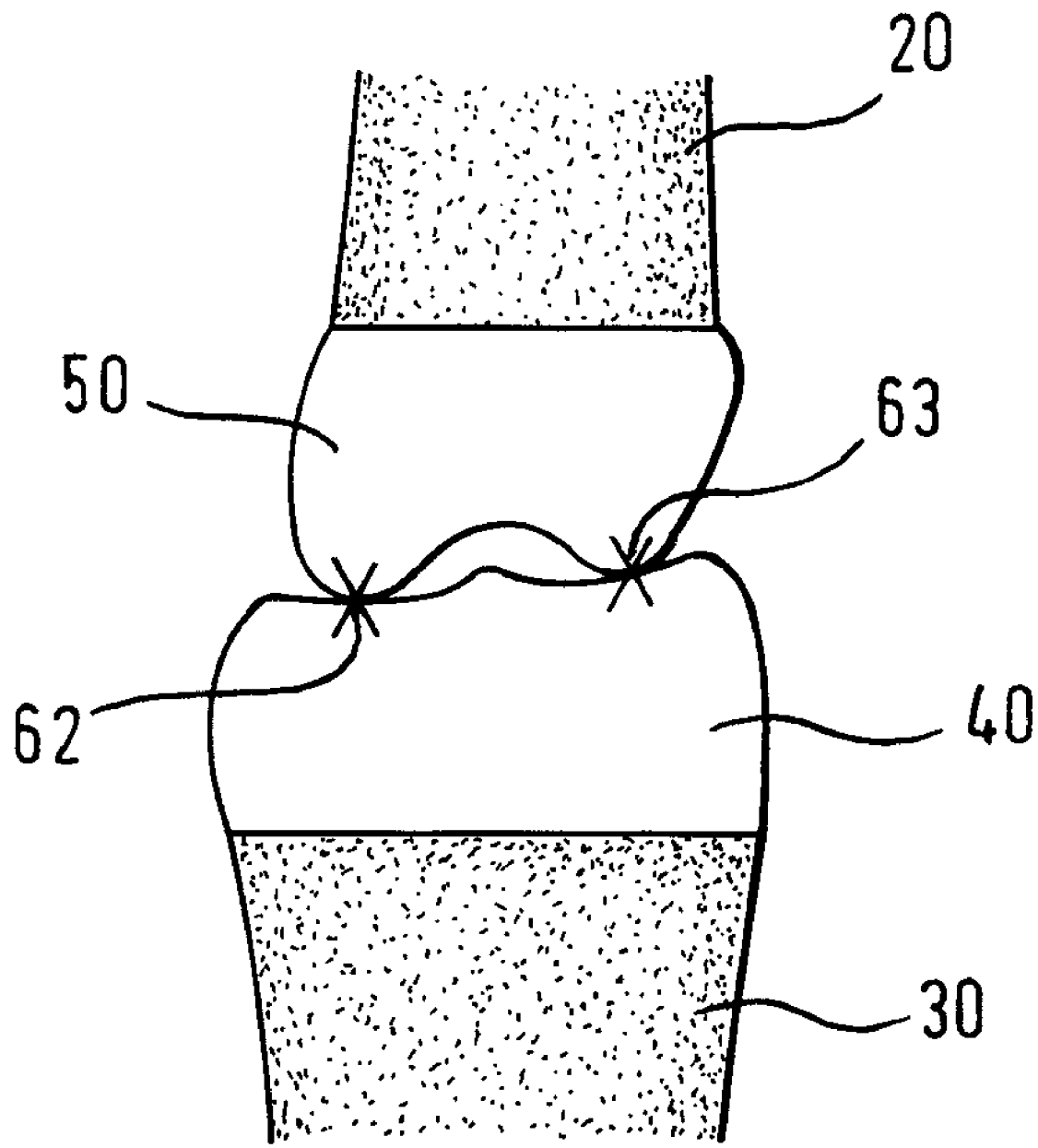
FIG. 3 shows contact points between a femur implant and a tibia implant.

FIG. 3 shows the tibia 30 and the femur 20 as well as the tibia implant 40 and the femur implant 50 which represent the virtual placement of the implants. Preferably, the position of the femur implant 50 is matched and/or adjusted to the envelope points such that the implants 40 and 50 virtually touch each other at points 62 and 63 for each relative pose.

For each of the poses of the plurality of poses the touch points 62, 63 in the reference system of the tibia represent a plurality of points in the reference system of the femur. These points are called envelope points.

After having determined the envelope points, the femur implant is virtually placed. In other words, a representation of the first implant in the first reference system is placed. This placement is done such that the femur implant is adjusted or matched relative to the plurality of envelope points preferably, such that the femur implant contacts the envelope points as close as possible so that in case of movement, the envelope points represent the touch points between the femur and the tibia. Of course, it is up to the surgeon, to deviate from this proposal for placement which is a result of the virtual planning according to the present invention.

Preferably during data acquisition of the relative poses, i.e. during the flexion movements, a relative rotation of the limb axis, i.e. of the tibia axis and the femur axis, is calculated and shown to the surgeon. This allows the surgeon to keep the relative rotation within a predetermined range. This predetermined range may be described by degrees of relative rotation of the limb axis. The upper limit of the range may be between 0 and 10 degree, preferably between 1 and 5 degree, preferably between 2 and 4 degree, preferably about 3 degree. For calculating the relative rotation of a limb axis, the situation in extension of the limbs may be used as a starting point. In extension, there is generally no relative rotation of the limbs. If, starting from the full extension, there is a flexion movement, then in a pose where there is flexion, a relative rotation of one of the reference systems with respect to the limb axis fixed in the other reference system may be calculated. The relative rotation describes the rotational degree with respect to the starting situation, i.e. the situation of full extension.

Figure 4:
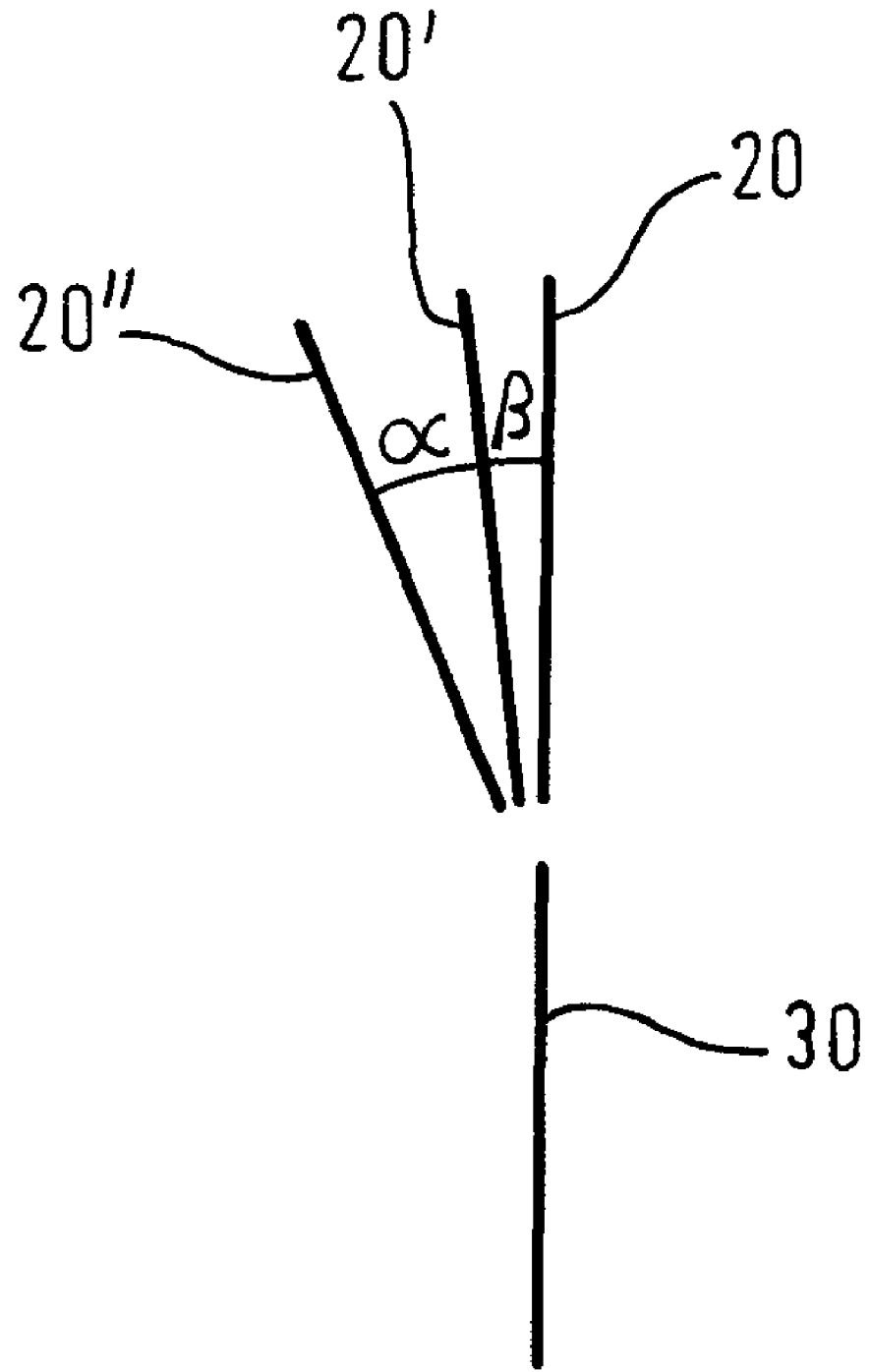
FIG. 4 shows different situations of deformation of the limb joint.

As mentioned above, the relative pose data may be acquired by relative movement of the limbs. There may be a pre-operative deformity of the joint. We assume that this pre-operative deformity may be corrected by external force to be within a predetermined, i.e. an acceptable range. During acquiring of the relative pose data this external force may be applied in order to assure that all relative pose data relate to a situation of corrected deformity. Alternatively, the situation as shown in FIG. 4 may be given. In FIG. 4 the femur axis 20 is shown in case of no deformity. Furthermore, the position of femur axis 20' is shown for deformation after appliance of force where the deformation is acceptable. For instance, the degree of deformation is 20. The position of the femoral axis 20" shows a situation where there is a deformation before appliance of force, i.e. no corrected deformation. The angle α between the location 20' and 20" may be detected as described in the parallel application. The angle α describes the difference between the uncorrected relative pose (forceless situation) and the corrected relative pose (force situation). This detected angle α may be used to calculate the relative pose data in case the relative movement is performed without applying a correction force in order to correct the deformity. If uncorrected relative pose data (representing the relative pose between the reference systems) are acquired by relative movement of the limbs without external force (i.e. without correction of deformation), this data may be used in order to calculate corrected relative pose data which describes the situation where the deformity is corrected to be within an acceptable range. This may be done by using the angle α for distance determined in case of extension of the limbs and to correct the relative pose based on this angle α in order to virtually place the axis 20" to the position 20'.

Figure 5:
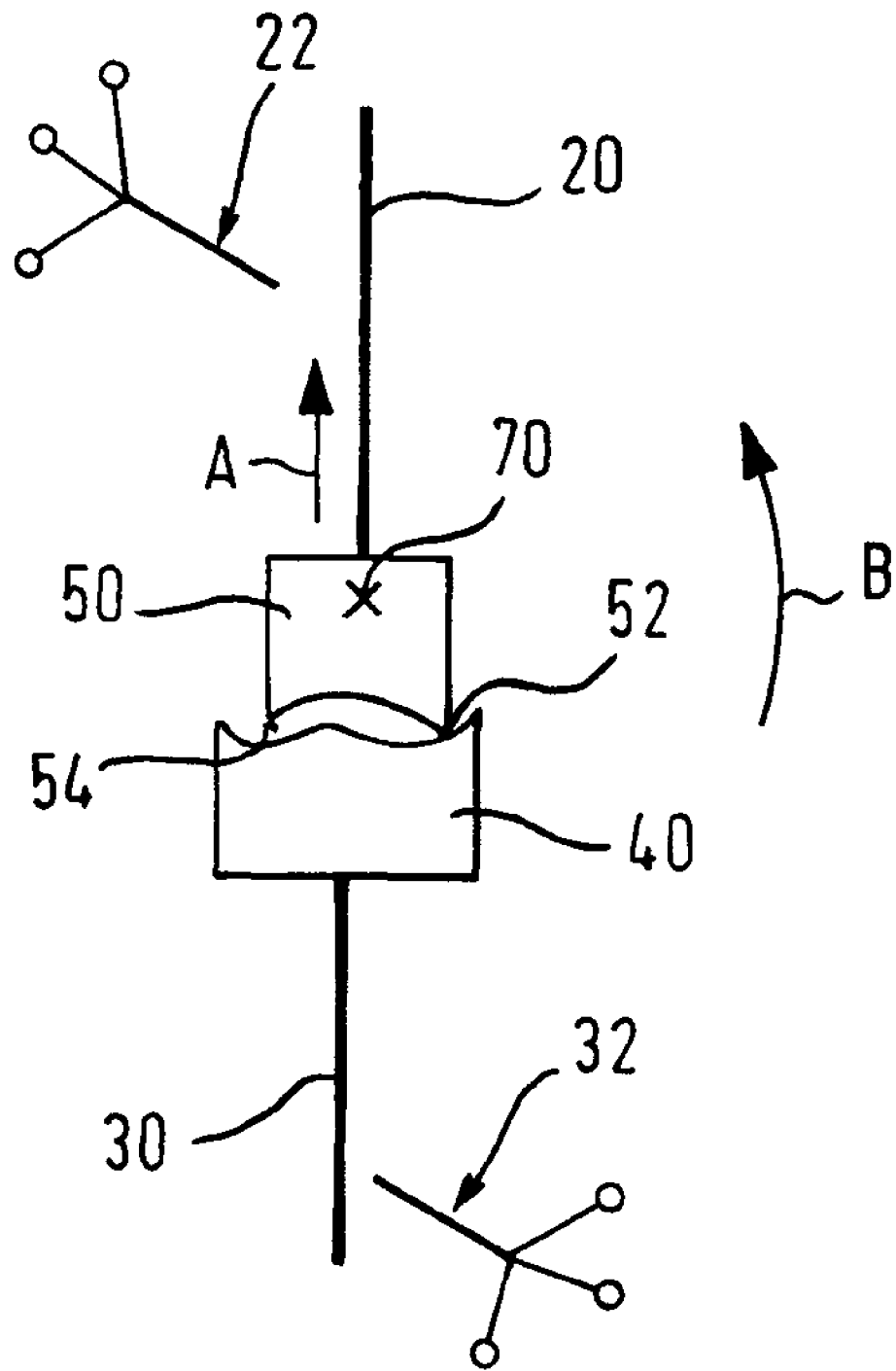
FIG. 5 shows virtual relative movements of the femur implant relative to the tibia implant.

When the femur implant is adjusted to the tibia implant, this is preferably done by virtually rotating the femur implant 50 around an axis 70 which is perpendicular to the femur axis 20 shown in FIG. 5. Preferably, this axis penetrates virtually the femur implant 50. This rotation movement is called a tilting movement of the femur implant. Furthermore, in addition to the virtual tilting movement, a virtual translational movement along the axis 20 is preferably performed by the virtual implant 50. Preferably at the beginning of the adjustment process, the implant 50 is placed at a predefined position relative to the femur axis 20. Then, a virtual tilting movement and translational movement is performed until a preferred relative position between contact points 52 and 54 of the femur implant and the envelope points is achieved. In particular, a position is selected and preferred to be determined where the contact points 52 and 54 of the femur implant 50 contact the envelope points. The tilting movement is shown by the arrow B in FIG. 5 and the translational movement by the arrow A in FIG. 5.

The contact points 52 and 54 of the femur implant 50 are predetermined points which are selected to be most appropriate to contact the envelope points.

In the above described manner, the position of the femur implant is determined relative to the position of the tibia implant. Based on the position of the femur implant and the tibia implant as well as based on shape and size of the implants, cutting planes may be planned. The surgeon may later use the planned cutting planes in order to cut the tibia and the femur along the planes and to then attach the implants to the tibia and the femur. Preferably, according to the invention, a so-called "joint line" is calculated based on the planned location of the femur implant and the tibia implant. This joint line describes an axis of rotation in case of a flexion movement of the limbs. Preferably, the method of the present invention joint allows the user or surgeon to move the joint line to a different position. Based on the displacement of the joint line and based on the previous location of the virtual femur implant and tibia implant, the planning method of the present invention calculates the new and displaced position of the femur implant and the tibia implant.

Preferably, according to a further embodiment of the invention, the implants are selected out of a plurality of virtual candidate implants based on the adjusting process of the femur implant to the tibia implant. For instance, a tibia implant is selected by a surgeon. Based on this selected virtual tibia implant, the contact or surface points 62 and 63 are determined. Based on the envelope points determined for this contact or surface points 62 and 63, a femur implant is selected out of the plurality of virtual candidate femur implants which selected femur implant allows for best adjustment of the femur implant to the envelope points. The selection procedure may be based on a calculation of deviation of the femur implant from the envelope points for the different candidate virtual femur implants. That femur implant is selected out of the candidate femur implants for which the minimal deviation has been calculated.

An exemplary method for pre-operatively determining a degree of deformity of an anatomical structure joining to limbs may be used to determine a degree of deformity of an anatomical joint, e.g. a knee-joint joining femur and tibia, respectively or of an elbow joint. In particular, the above mentioned correction degree or correction vector may be determined as described in the following.

A degree of deformity of an anatomical structure joining two limbs comprises the relative angular orientation or angular difference of axis corresponding to the two limbs.

The degree of deformity is measured in angular degrees. An angular difference of a predetermined angle, e.g. of up to 3° or 4° may be considered as a mild deformity. An angular difference greater than the predetermined angle but lower than another higher predetermined angle, e.g. between 3° and 5° or 4° and 6° may be considered as a moderate deformity.

The deformity may comprise varus and valgus deformity.

An exemplary method may comprise the step of providing data representing the pose of an axis of a limb in a reference system in which the limb is fixed.

A reference system in which a limb is fixed, i.e. representing poses of the limb, may be provided by a marker array fixedly coupled to the limb, as described above. This marker array is also called reference array.

In order to provide data representing a pose of an axis of a limb in a reference system in which the limb is fixed, an additional locating device or locating devices (e.g. pointers) are brought into selected poses determining the axis and measured in the reference system in which the limb is fixed, as described above.

An exemplary method may provide data representing poses of a first limb (e.g. femur) in a first reference system in which the first limb is fixed and of a second axis of the second limb (e.g. tibia) in a reference system in which the second limb is fixed, the first and second limb being joined by an anatomical structure, e.g. the knee joint.

An exemplary method may further comprise the step of providing pose orientation data representing a relative pose between the first and second reference system with the first and second limb in extension, and with an external force being applied to eliminate or reduce the deformity of the anatomical structure. An external force may be applied to the first and second limb in extension in order to at least partially compensate the deformation of the anatomical structure.

An exemplary method may further comprise the step of determining a relative angular orientation between the first axis of the first limb and the second axis of the second limb based on the force orientation data, said relative angular orientation being referred to as force relative angular orientation. Determining a relative angular orientation between the first and second axis from force orientation data may comprise determining a relation between the first and second reference system with the first and second limb in extension, and with an external force being applied.

In an exemplary method, a relative angular orientation may comprise components related to planes, e.g. a sagittal and/or coronal component. Splitting the relative angular orientation into components may simplify the assessment of a degree of deformity of the anatomical structure.

An exemplary method may further comprise the step of comparing force relative angular orientation with a relative angular orientation which is used as a reference.

An exemplary method may further obtain the reference relative orientation by the step of providing forceless orientation data representing a relative pose between the first and second reference system with the first and second limb in extension and without an external force being applied. The pose of a limb in a reference system may be represented by the pose of an axis of the limb and/or by poses of landmarks of the limb. An axis of the limb is in particular a characteristic axis of the limb along the extension of the limb.

An exemplary method may obtain the reference relative angular orientation by the further step of determining the reference relative angular orientation, i.e. a forceless relative angular orientation, between the poses of the limbs e.g. between the first axis of the first limb and the second axis of the second limb based on forceless orientation data. A method according to the invention may be executed by a computer program loaded by executed on a general purpose computer, a dedicated computer or a computer on a chip.

An exemplary method may obtain a difference vector between the force relative angular orientation and the forceless relative angular orientation in order to obtain the correction degree or correction vector suitable to virtually correct a pre-operative deformity of the anatomical structure joining the first and second limb.

The invention claimed is:

1. A computer-implemented method for planning implant placement, the implant comprising a first implant in a first limb and a second implant in a second limb, the first and the second implant forming an artificial structure joining the first and second limb, the method comprising the steps:
   a) providing a first limb data set representing a first reference system in which the first limb is fixed;
   b) providing a second limb data set representing a second reference system in which the second limb is fixed;
   c) providing a representation of the implant for the head of the second limb in a known position in the second reference system;
   d) providing relative pose data representing a plurality of different positions and/or orientations, referred to as relative poses, of the first reference system relative to the second reference system;
   e) determining, using a processor, a data set representing a plurality of envelope points, said envelope points being generated by calculating for the plurality of relative poses locations of a point of the representation of the implant provided in step c in the first reference system; and
   f) placing, using a processor, a representation of the first implant in the first reference system by adjusting and/or matching pose of the representation of the first implant to the plurality of envelope points.

2. Method according to claim 1, wherein one representation out of a plurality of representations of first implants is placed in the first reference system and is adjusted and/or matched with respect to the plurality of envelope points and out of the plurality of representations of first implants that representation is selected for which a desired adjustment and/or matching is achievable.

3. Method according to claim 1 wherein the plurality of envelope points are calculated by correcting the location of the point of the a second implant representation in the first reference system for the plurality of relative poses in case of an uncorrected deformity of the anatomical limb by means of a correction vector which describes the correction of the relative pose of the first and second reference system in case of a corrected deformity.

4. Method according to claim 1 wherein providing relative pose data representing the plurality of different poses of the first and second reference system comprises detecting reference arrays attached to the first limb and the second limb during movement of the second limb relative to the first limb, said movement includes flexing and/or extending the second limb relative to the first limb.

5. Method according to claim 1 wherein the implant placement is suitable for total knee arthroplasty, the artificial structure joining the first and second limb comprises an artificial knee joint and the first and second limb comprises femur and tibia, respectively.

6. Method according to claim 1 wherein the placing step further comprises:
   displacing the representation of the first implant along an axes of the first limb and/or tilting the representation of the first implant relative to the axis of the first limb.

7. Method according to claim 1 the method further comprising:
   registering an axis of the first limb in the first reference system and an axis of the second limb in the second reference system.

* * * * *